(12) United States Patent
Lin et al.

(10) Patent No.: US 7,405,317 B2
(45) Date of Patent: Jul. 29, 2008

(54) PHOSPHATE-BEARING PRODRUGS OF SULFONYL HYDRAZINES AS HYPOXIA-SELECTIVE ANTINEOPLASTIC AGENTS

(75) Inventors: Xu Lin, Branford, CT (US); Ivan King, North Haven, CT (US); Michael F. Belcourt, Wallingford, CT (US); Terrence W. Doyle, Killingworth, CT (US)

(73) Assignee: Vion Pharmaceuticals Inc., New Haven, CT (US)

( * ) Notice: Subject to any disclaimer, the term of this patent is extended or adjusted under 35 U.S.C. 154(b) by 0 days.

(21) Appl. No.: 11/232,252

(22) Filed: Sep. 21, 2005

(65) Prior Publication Data

US 2006/0089332 A1    Apr. 27, 2006

Related U.S. Application Data

(60) Provisional application No. 60/611,623, filed on Sep. 21, 2004, provisional application No. 60/616,500, filed on Oct. 6, 2004, provisional application No. 60/615,419, filed on Oct. 1, 2004.

(51) Int. Cl.
  C07F 9/22      (2006.01)
  C07C 313/04    (2006.01)
  C07C 313/06    (2006.01)

(52) U.S. Cl. .................... 558/61; 562/8; 558/154; 558/193; 558/190

(58) Field of Classification Search ............ 514/79, 514/89, 114; 546/22; 548/111; 558/193, 558/154, 61; 562/8
See application file for complete search history.

(56) References Cited

U.S. PATENT DOCUMENTS

| | | | |
|---|---|---|---|
| 4,684,747 A | 8/1987 | Sartorelli et al. | |
| 4,849,563 A | 7/1989 | Sartorelli et al. | |
| 5,101,072 A | 3/1992 | Sartorelli et al. | |
| 5,214,068 A | 5/1993 | Sartorelli et al. | |
| 5,256,820 A | 10/1993 | Sartorelli et al. | |
| 5,637,619 A | 6/1997 | Sartorelli et al. | |
| 5,767,134 A | 6/1998 | Li et al. | |
| 6,040,338 A | 3/2000 | Sartorelli et al. | |
| 6,458,816 B1 | 10/2002 | Doyle et al. | |
| 6,855,695 B2 * | 2/2005 | Lin et al. | 514/12 |

OTHER PUBLICATIONS

Hockel et al., Cancer Res. 1991, 51:6098.
Brizel et al., Radiother Oncol. 1999, 53:113.
Stratford et al, Anticancer Drug Des. 1998, 13:519.
Ashur-Fabian et al., Proc. Natl. Acad. Sci. USA 2004. 101:12236.
Yang et al., Cancer Res. 2003, 63:1520.
Korbelik et al., Mutal. Res. 1980, 78:201.
Shealy et al., J. Med. Chem. 1984, 27:664.
Shyam et al., J.Med. Chem. 1999, 42:941.
Seow et al., Proc. Natl. Acad. Sci. USA 2005, 102:9282.
Shyam et al., J. Med. Chem. 1993, 36:3496.
Shyam et al., J. Med. Chem. 1996, 39:796.
Majer et al., J. Org. Chem. 1994, 59:1937.
Pridgen et al., J. Org. Chem. 1989, 54:3231.
Matulic-Adamic et al., J. Org. Chem. 1995, 60:2563.
Durgam et al., J. Med. Chem. 2005, 48:4919.
Jansson et al., Tetrahedron Lett. 1986, 27:753.
Mathre et al., J. Org. Chem. 1993, 58:2880.
Brown et al., J. Am. Chem. Soc. 1988, 110:1539.
Ramachadran et al., Tetrahedron: Asymm. 5: 1061.
Ohkuma et al., J. Am. Chem. Soc. 1998, 120:13529.
Baar et al., J. Am. Chem. Soc. 2004, 126:8216.
Silverberg et al., Tetrahedron Lett. 1996, 37:771.

* cited by examiner

Primary Examiner—Rebecca Anderson
Assistant Examiner—Yong Chu
(74) Attorney, Agent, or Firm—Henry D. Coleman; R. Neil Sudol; William J. Sapone

(57) ABSTRACT

Novel phosphate-bearing prodrugs of sulfonyl hydrazines have the formula presented below. Pharmaceutical compositions and uses thereof in the treatment of cancer are claimed. The aforementioned prodrugs include enantiomers, stereoisomers and tautomers thereof, as well as pharmaceutically acceptable salts or solvates and metabolites from all stages. The aforementioned prodrugs are preferentially activated in hypoxic tumors and can be given either alone, or in combination with other anticancer agents or with phototheraphy or radiotherapy.

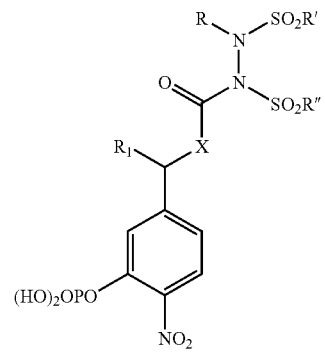

where R is $C_1$-$C_{10}$ alkyl or haloalkyl;
R' and R" are each independently $C_1$-$C_{10}$ alkyl;
$R^1$ is $CH_3$; and
X is O;
or a pharmaceutically acceptable salt, solvate, polymorph or metabolite thereof.

11 Claims, 9 Drawing Sheets

PHOSPHATE-BEARING PRODRUGS OF SULFONYL HYDRAZINES AS HYPOXIA-SELECTIVE ANTINEOPLASTIC AGENTS

RELATED APPLICATIONS

This application claims priority from U.S. provisional application No. 60/611,623, filed Sep. 21, 2004; U.S. provisional application No. 60/615,419, filed Oct. 1, 2004; and U.S. provisional application No. 60/616,500, filed Oct. 6, 2004, each of which applications is incorporated by reference herein in its entirety.

FIELD OF THE INVENTION

The present invention relates to metabolically activated sulfonyl hydrazine prodrugs (SHPs) exhibiting anti-tumor activity in mammals. Methods of treating neoplasia, especially including cancer are additional aspects of the present invention.

BACKGROUND OF THE INVENTION

Eradication of solid tumors requires strategies that address the viable populations of malignant cells within hypoxic regions of such tumors. An insufficient and poorly organized vasculature, a major characteristic of rapidly growing tumor masses, results in poor oxygenation, high interstitial pressure, and a population of cells that are hypoxic, quiescent or slowly cycling, and distal to the blood supply, thus inadequate vascularization in solid tumors results in low oxygen and being difficult to reach with cytotoxic levels of drugs (Hockel, et al. *Cancer Res.* 1991, 51: 6098). Radiotherapy is thus ineffective in these areas as the radiation fails to generate sufficient oxygen radicals to result in cytotoxicity (Brizel, et al. *Radiother Oncol.* 1999, 53: 113). Moreover, the activity of cytotoxic drugs is also attenuated. Thus cells from these regions are frequently responsible for the re-establishment of disease. After treatment with oxygen-dependent cytotoxins such as x-irradiation, which generates oxygen radicals that damage cellular DNA, and conventional chemotherapeutics that target the well-oxygenated, rapidly growing portion of the tumor mass, the resistant hypoxic cell fraction can repopulate the tumor (Stratford, et al. *Anticancer Drug Des.* 1998, 13: 519). Moreover, hypoxic cells are subjected to an environment that enhances the selection of mutations which cause the progression of the neoplasm towards an increasingly aggressive phenotype. For example, hypoxia selects for cells deficient in p53-mediated apoptosis, enhances mutation rates, upregulates genes involved in drug resistance, angiogenesis, and tumor invasiveness (including HIF-1α), and thus is associated with a more metastatic phenotype (Ashur-Fabian, et al. *Pro Natl Acd Sci USA.* 2004, 101: 12236).

Prodrugs that act as hypoxia-selective cytotoxins generally must be substrates for one electron reductases such as NADPH:cytochrome (P450) reductase. The one-electron reduced prodrug radical, in the presence of oxygen, redox cycles back to the parent prodrug, preventing progression of the activation cascade and release of the cytotoxic, DNA damaging species. Under hypoxic conditions, further reduction of the radical anions alters the chemistry of the prodrug to allow release of the cytotoxic species (Yang, et al. *Cancer Res.* 2003, 63: 1520). Nitroaromatic and nitroheterocyclic compounds readily undergo one electron reduction to nitro radical anions (Korbelik, et al. *Mutal Res,* 1980, 78: 201). These molecules react rapidly with oxygen to regenerate the parental molecule. However in the absence of oxygen they are reduced further to generate hydroxylamine derivatives and then final aniline forms. While the nitro group is highly electron withdrawing, the hydroxylamine group is strongly electron donating. This results in a major change in the chemistry of the aromatic or heterocyclic ring, triggering the activation cascade and the release of parent drug.

As alkylating agents, a novel series of 1,2-bis(sulfonyl) hydrazine prodrugs (SHPs) with the ability to generate active chloroethylating species had been developed recently (Sartorelli, et al. U.S. Pat. No. 006,040,338, 2000; U.S. Pat. No. 005,637,619, 1997; U.S. Pat. No. 005,256,820, 1993; U.S. Pat. No. 005,214,068, 1993; U.S. Pat. No. 005,101,072, 1992; U.S. Pat. No. 004,849,563, 1989; and U.S. Pat. No. 004,684,747, 1987). The anti-tumor activity has been suggested to result from chloroethylating and subsequent cross-linking of DNA (Shealy, et al., *J Med Chem.* 1984, 27: 664).

1,2-Bis(methylsulfonyl)-2-(2-chloroethyl)-hydrazine carboxylic acid 1-(4-nitrophenyl)ethyl ester (KS119), the current lead compound in the SHP series, requires enzymatic nitro-reduction to generate the alkylating species 90CE, as demonstrated in FIG. 1. Thus, KS119 takes advantage of the hypoxic, reductive environment of solid tumors, thus creating an exploitable difference between cells in normal, well oxygenated tissues and hypoxic neoplastic cells (Shyam, et al. *J Med Chem.* 1999, 42: 941; and Seow, et al. *Proc Natl Acad Sci USA.* 2005, 102: 9282).

However, KS119 is rather insoluble in aqueous solution, even it has not sufficient solubility (<5 mg/mL) in co-solvent system like polyethylene glycol (PEG) and ethanol in order to meet clinical requirements of this drug. Therefore, our aim was to synthesize analogs of KS119 that (a) were capable of improving its water-solubility and stability in aqueous solution at pH 3 to 8; (b) were capable of forming chloroethylating species; and (c) were capable of maintaining hypoxia-selective activation.

Turning to the present invention, we believe that water-soluble compounds according to the present invention satisfy the above conditions. An example of such an SHP (KS119W) would be the phosphate-containing analog of KS119 shown in FIG. 2 for the following reasons:

(a) In general, a phosphate-bearing analog, including its salt form should have good water-solubility and stability at neutral pH;

(b) The bioconversion of compounds according to the present invention proceeds via alkaline phosphatase (AP) cleavage of the oxygen-phosphorous bond to form the phenol intermediate, as shown in FIG. 2.

(c) The bioconversion of the 2-nitrophenol intermediate is selectively activated under conditions of hypoxia to generate a hydroxylamine derivative or aniline form.

(d) The above intermediate of the amino analogs subsequently undergo fragmentation resulting in the formation of chloroethylating species (90CE). Release of 90CE would only occur on reduction of the nitro group under conditions of hypoxia.

(e) Compounds of the present invention are considered as prodrugs of 90CE that has been identified as an alkylating agent against a broad anticancer spectrum of neoplastic disease states, including, for example, numerous solid tumors.

OBJECTS OF THE INVENTION

In one aspect of the invention, an object of the present invention is to provide compounds, pharmaceutical compositions and methods for the treatments of neoplasia, including animal and human cancer.

In another aspect of the invention, an object of the present invention is to provide methods of treating neoplasia utilizing compositions that exhibit favorable anti-cancer characteristics in hypoxia conditions and enhanced characteristics of activity, pharmacokinetics, bioavailability and reduced toxicity.

It is yet another object of the invention to provide compositions and methods for the treatment of cancers which are resistant to treatment with traditional chemotherapeutic agents, and for treatment of cancers by combination with other anticancer agents or with phototheraphy or radiotherapy.

One or more of these and/or other objects of the invention may be readily gleaned from the description of the invention that follows.

BRIEF DESCRIPTION OF THE INVENTION

The present invention is directed to compounds according to structures I or II:

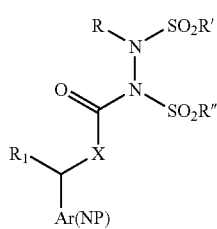

structure I

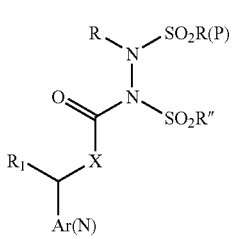

structure II

Where R is $C_{1-10}$ alkyl, or $C_{1-10}$ haloalkyl;
R' or R" is $C_{1-10}$ alkyl, or $C_{5-20}$ aryl or heteroaryl;
$R_1$ is H; $C_{1-10}$ alkyl, $C_{1-10}$ alkoxyl;
X is O, NH, or NR;
R(P) is a phosphate-bearing alkyl group, for example, R(P) is Y'OPO(OH)$_2$ where Y is $(CH_2)_n$, $O(CH_2)_n$, $NH(CH_2)_n$, $NR(CH_2)_n$, n is 1-5; Y is aryl or heteroaryl;

Ar(N) is a nitro-containing aryl group, for example,

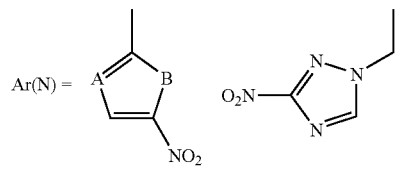

where A is CH, CR, or N; and B is CH=CH, O, S, NH, or NR; and
Ar(NP) is a phosphate-bearing and nitro-containing aryl group, for examples,

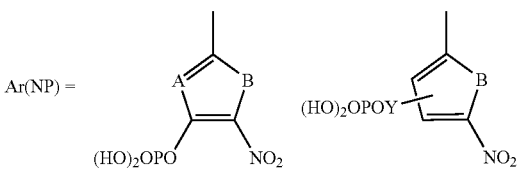

where A is CH, CR, or N; and B is CH=CH, O, S, NH, or NR; and
Y is $(CH_2)_n$, $O(CH_2)_n$, $NH(CH_2)_n$, $NR(CH_2)_n$, $OCOO(CH_2)_n$, $NHCOO(CH_2)_n$;
n is 1-5.

The present invention is also directed to compounds according to formulas I, II, III and IV

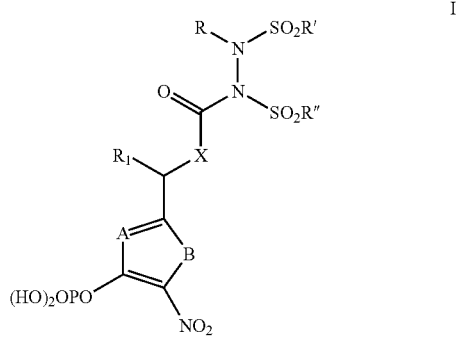

I

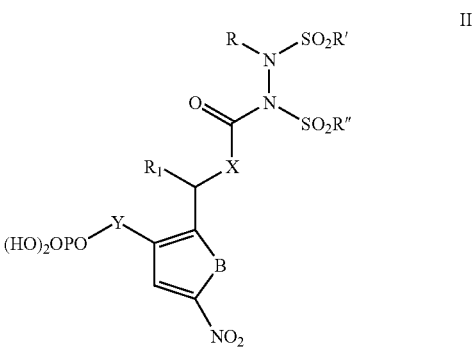

II

-continued

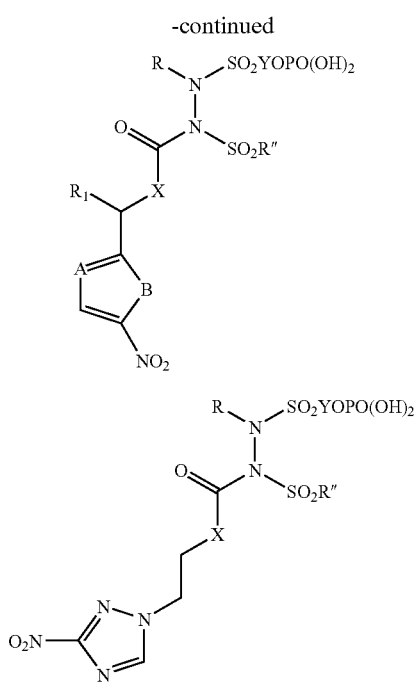

Where R=$C_{1-10}$ alkyl, or $C_{1-10}$ haloalkyl (preferably containing no more than 5 halogen groups, preferably 2-chloroethyl);

R' and R" are independently $C_{1-10}$ alkyl, or $C_{5-20}$ aryl or heteroaryl (preferably methyl);

$R_1$ is H, $C_{1-10}$ alkyl, $C_{1-10}$ alkoxyl, $C_{5-20}$ aryl or heteroaryl or $C_{5-20}$ aroxyl or heteroaroxyl (preferably methyl and ethyl);

X is O, NH, or NR (preferably O);

Y is $(CH_2)_n$, $O(CH_2)_n$, $NH(CH_2)_n$, $NR(CH_2)_n$, $OCOO(CH_2)_n$, $NHCOO(CH_2)_n$; n=1, 2, 3, 4 or 5 (preferably n=2 and 3); or Y=aryl or heteroaryl (preferably para-phenyl);

A=CH, or N (preferably CH); and

B=CH=CH, O, S, NH, or NR (preferably CH=CH); or pharmaceutically acceptable salts, solvates, polymorphs or metabolites, thereof.

In preferred aspects, the present invention relates to compounds according to structure IA:

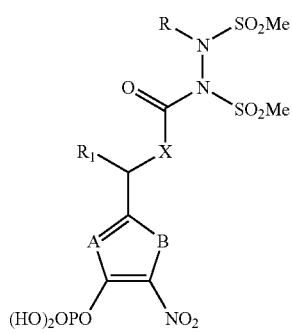

Structure IA

Where R=$C_{1-10}$ alkyl, or $C_{1-10}$ haloalkyl; $R_1$=H; $C_{1-10}$ alkyl, $C_{1-10}$ alkoxyl; X=O, NH, or NR; A=CH, CR, or N; and B=CH=CH, O, S, NH, or NR.

The aforementioned compounds include enantiomers, stereoisomers and tautomers thereof, as well as pharmaceutically acceptable salts, solvates, polymorphs and metabolites from all stages.

Preferred agents in the compounds are 4-nitrophenyl series of compound structure IA where A is CH; B is CH=CH; X is O; R is $CH_2CH_2Cl$; $R_1$ is $CH_3$; a phosphate group can be free acid or salt (preferably Tris). In particularly preferred aspects of the hydrazine-carboxylic acid 1-(4-nitrophenyl)ethyl ester (KS119W), R-configuration structure (VNP40541) of the enantiomers is more preferable.

Compounds according to the present invention and especially the preferred compositions according to the present invention, as set forth above, are extremely effective compounds for the treatment of neoplasia. They also exhibit at least one or more improvements such as an enhanced anti-neoplasia activity, a reduced toxicity, a higher water-solubility, or a more favorable pharmacokinetic profile compared to KS119.

These compounds according to the present invention are preferentially activated in hypoxic tumors and can be given either alone, or in combination with other anticancer agents or with phototheraphy or radiotherapy.

Compounds according to the present invention may be used in pharmaceutical compositions for the treatment of cancer, as well as a number of other conditions and/or disease states. Examples according to the present invention may be as intermediates in the synthesis of other compounds exhibiting biological activity as well as standards for determining the biological activity of the present compounds. In some applications, the present compounds may be used for treating microbial infections, especially including viral, bacterial, and fungal infections. These compounds comprise an effective amount of any one or more of the compounds disclosed hereinabove, optionally in combination with a pharmaceutically acceptable additive, carrier, or excipient.

A further aspect of the present invention relates to the treatment of cancer, comprising administering to a patient in need thereof an effective amount of a compound as described hereinabove, optionally in combination with a pharmaceutically acceptable additive, carrier, or excipient. The present invention also relates to methods for treating neoplasia in mammals comprising administering an effective amount of a compound as described hereinabove to a patient suffering from cancer. The treatment of solid malignant tumors, leukemia, and lymphomas comprising administering to a patient an anti-tumor effective amount of one or more these agents is a preferred embodiment of the present invention. The treatment of various other related disease states may also be effected using the compounds of the present invention. This method may also be used in comparison tests such as assays for determining the activities of related analogs as well as for determining the susceptibility of a patient's cancer to one or more of the compounds according to the present invention.

BRIEF DESCRIPTION OF THE FIGURES AND TABLES

DETAILED DESCRIPTION OF THE INVENTION

Figure 1:
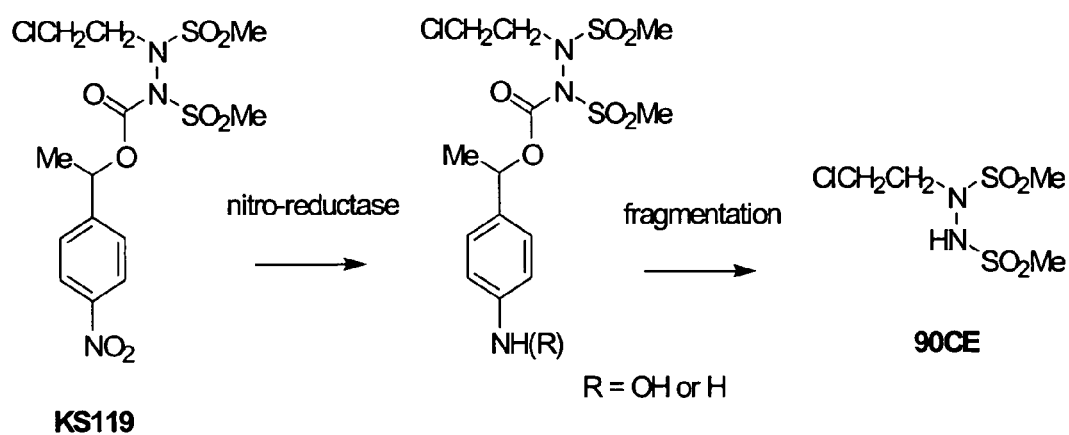
FIG. 1 is a representation of a suggested mechanism of activation of KS119.

The following terms shall be used throughout the specification to describe the present invention.

The term "patient" is used throughout the specification to describe an animal, including a mammal and preferably a human, to whom treatment, including prophylactic treatment, with the compositions according to the present invention is provided. For treatment of infections, conditions or disease states which are specific for a specific animal such as a human patient, the term patient refers to that specific animal.

The term "effective amount" is used throughout the specification to describe concentrations or amounts of compounds according to the present invention which may be used to produce a favorable change in the disease or condition treated, whether that change is a remission, a decrease in growth or size of cancer or a tumor, a favorable physiological result, a reduction in the growth or elaboration of a microbe, or the like, depending upon the disease or condition treated.

The term "compound", as used herein, unless otherwise indicated, refers to any specific chemical compound disclosed herein. Within its use in context, the term generally refers to a single compound, but may also refer to stereoisomers and/or optical isomers (including racemic mixtures), well as specific enantiomers, or enantiomerically enriched mixtures of disclosed compounds, as well as tautomers.

The term "neoplasia" is used throughout the specification to describe the pathological process that results in the formation and growth of a neoplasm, i.e., an abnormal tissue that grows by cellular proliferation more rapidly than normal tissue and continues to grow after the stimuli that initiated the new growth cease. Neoplasia could be a distinct mass of tissue that may be benign (benign tumor) or malignant (carcinoma). As used herein, the term neoplasia is used to describe all cancerous disease states and embraces or encompasses the pathological process associated with malignant hematogenous, ascitic, and solid tumors. The term "cancer" and the term "tumor" used in this application is interchangeable with the term "neoplasia".

Cancer which may be treated using compositions according to the present invention include, for example, stomach, colon, rectal, liver, pancreatic, lung, breast, cervix uteri, corpus uteri, ovary, prostate, testis, bladder, renal, skin, brain/CNS, head and neck, throat, Hodgkins disease, non-Hodgkins disease, multiple myeloma, acute lymphocytic leukemia, acute mylogenous leukemia, Ewings Sarcoma, choriocarcinoma, rhabdomyosarcoma, Wilms' tumor, neuroblastoma, hairy cell leukemia, mouth/pharynx, esophagus, larynx, melanoma, kidney and lymphoma, among others. The treatment of tumors comprising administering to a patient an anti-tumor effective amount of one or more these agents is a preferred embodiment of the present invention.

The term "alkyl" is used throughout the specification to describe a hydrocarbon radical containing between one to seven carbon units. Alkyl groups for use in the present invention include linear or branched-chain groups, such as preferably methyl, ethyl, propyl, isopropyl, butyl, isobutyl, tert-butyl, pentyl, isopentyl, hexyl, cylcohexyl, methylcyclopropyl and methylcyclohexyl.

The term "aryl" refers to a substituted or unsubstituted monovalent aromatic radical having a single ring (e.g., phenyl) or multiple condensed rings (e.g., naphthyl). The term "aroxyl" refers to an aryl group to which is bonded an alkoxy group, preferably through which another group is bonded (e.g. a sulfonyl group).

The term "heteroaryl" refers to heterocyclic aromatic ring groups having one or more nitrogen, oxygen, or sulfur atoms in the ring, such as imidazolyl, furyl, pyrrolyl, pyridyl, thienyl and indolyl. The term "heteroaroxyl" refers to a heteroaryl group to which is bonded an alkoxy group, preferably through which another group is bonded (e.g. a sulfonyl group).

The term "salt" is used throughout the specification to describe any salt consistent with the use of the compounds according to the present invention. In the case where the compounds are used in pharmaceutical indications, including the treatment of cancer, the term "salt" shall mean a pharmaceutically acceptable salt, consistent with the use of the compounds as pharmaceutical agents.

In preferred aspects, the present invention relates to compounds according to the structure (IA):

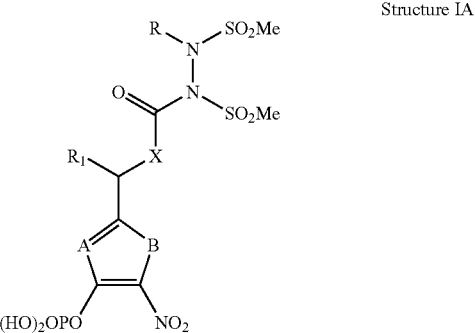

Structure IA

Where R=$C_{1-10}$ alkyl, or $C_{1-10}$ haloalkyl; $R_1$=H; $C_{1-10}$alkyl, $C_{1-10}$ alkoxyl; X=O, NH, or NR; A=CH, CR, or N; and B=CH=CH, O, S, NH, or NR.

Compounds according to the present invention include enantiomers, stereoisomers and tautomers thereof, as well as pharmaceutically acceptable salts, solvates, polymorphs and metabolites from all stages.

Figure 2:
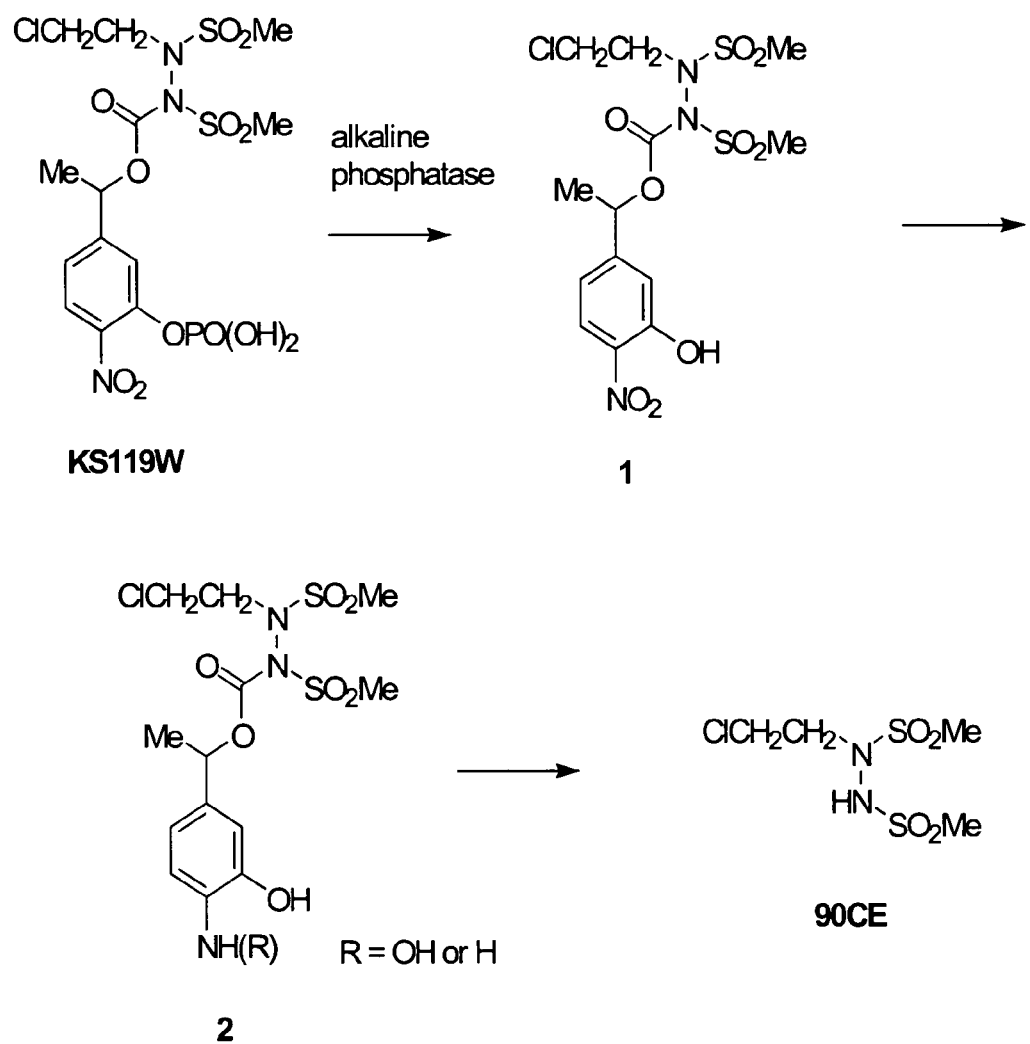
FIG. 2 is representations of a sample (KS119W) of the chemical embodiments and their proposed mechanism of activation in hypoxia conditions according to the present invention.

The present compounds represent prodrug forms of intermediates that are believed to exhibit their activity of DNA cross-linking through chloroethylation or methylation mechanisms. The rationale for the new prodrug design was that enzyme-activated prodrugs could be converted into active alkylating species (90CE) via a sequence of enzyme activations and prompt fragmentation. De-phosphorylation can be accomplished by alkaline phosphatase (AP) enzyme activation to give intermediate 1; nitro-reduction can be catalyzed by nitro reductase (NR) enzyme to form intermediate 2; and subsequent benzyl group fragmentation generated 9OCE, as shown in FIG. 2.

The compounds according to the present invention are preferentially activated in hypoxic tumors and can be given either alone, or in combination with other anticancer agents or with phototherapy or radiotherapy.

The compounds according to the present invention are primarily useful for their anti-neoplastic activity, including their activity against solid tumors. In addition, these compositions may also find use as intermediates in the chemical synthesis of other useful anti-neoplastic agents that are, in turn, useful as therapeutic agents or for other purposes, including use as standards for assays.

Preferred agents in the compounds are 4-nitrophenyl series where A is CH; B is CH=CH; X is O; R is $CH_2CH_2Cl$; $R_1$ is $CH_3$; a phosphate group can be the free acid or a salt. In particularly preferred aspects of the hydrazine-carboxylic acid 1-(4-nitrophenyl)ethyl ester (KS119W), the R-configuration structure (VNP40541) of the enantiomers is more preferably than S-configuration structure (VNP40551).

Compounds according to the present invention are synthesized by the adaptation of techniques that are well known in the art and are derived from 90CE. The synthesis of 90CE was published in two-step approach from 2-hydroxyethyl-hydrazine (See, Shyam, et al. *J Med Chem.* 1993, 36: 3496, also *J Med. Chem.* 1996, 39: 796). Analogs of compounds specifically described herein may be readily synthesized using the above general techniques and analogous synthetic methods available in the art without engaging in undue experimentation.

Figure 3:
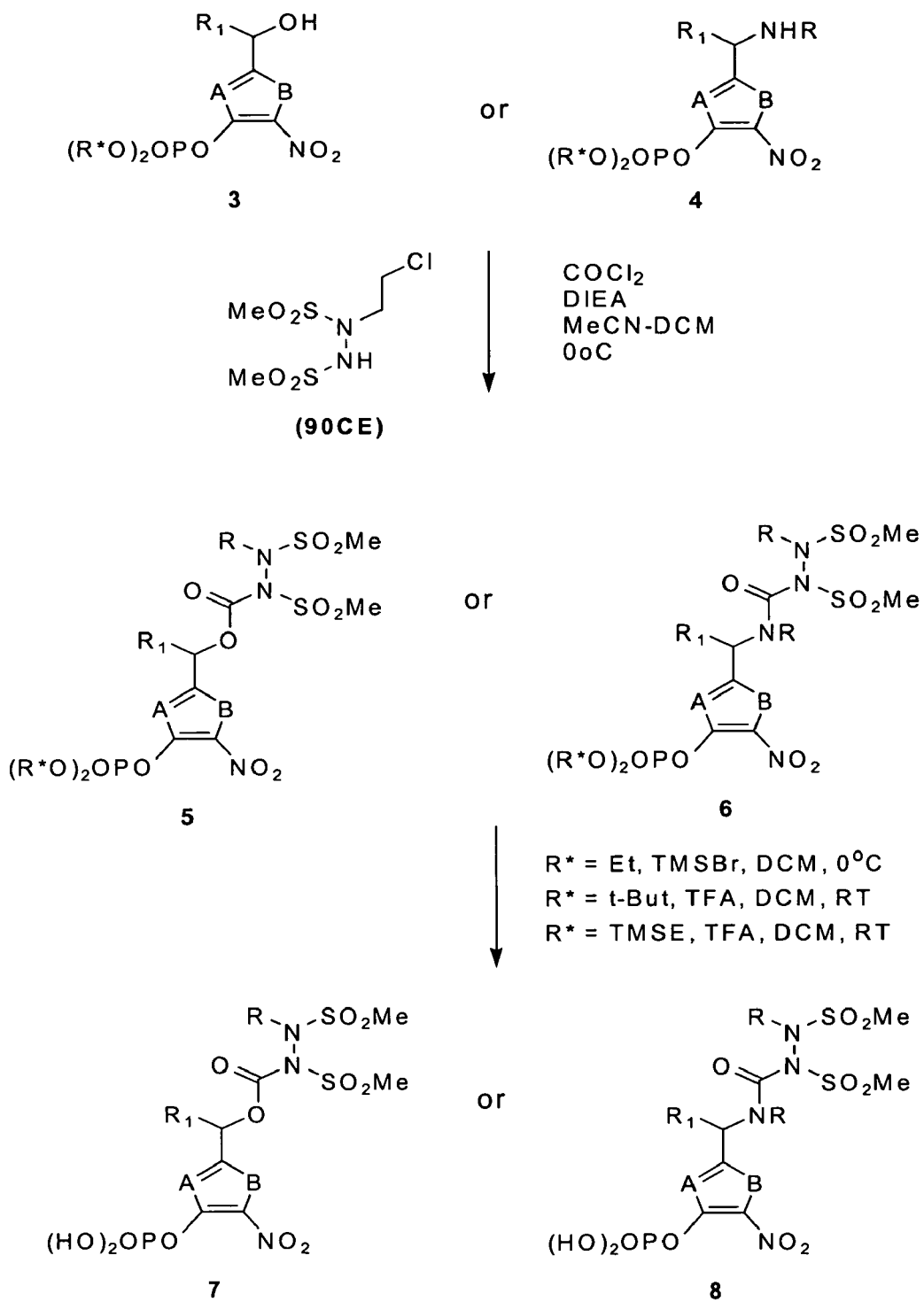
FIGS. 3 and 4 are representations of chemical schemes for synthesizing compounds according to the present invention.

By way of specific example, as demonstrated in FIG. 3, 1,2-bis(methylsulfonyl)-2-(substituted)hydrazine-carbonates of Compounds 1 (5, R=$CH_2CH_2Cl$) are synthesized respectively by reacting an appropriate α-alkyl 4-nitroarylmethyl alcohol or N-alkyl-N-(4-nitroarylmethyl)amine (3 or 4, where $R_1$ is —$CH_3$; R* is a protecting group of the phosphate group, such as diethyl or di-tert-butyl or 2-trimethylsilylethyl (TMSE) group with phosgene (20% toluene solution) or its equivalents, such as triphosgene or trichloromethyl chloroformate (see, Majer, et al. *J Org Chem.* 1994, 59: 1937; and Pridgen, et al. *J Org Chem.* 1989, 54: 3231), and a further condensation in situ with 90CE. This coupling reaction can be achieved in high yield while using N,N-diisopropylethylamine (DIPEA) as a base and keeping the reaction at 0° C. in dry acetonitrile-dichloromethane solvent overnight. The hydrazine-amides of Compounds I (6, R=$CH_2CH_2Cl$) can be synthesized by similar phosgene-coupling pathway (Lin, et al. U.S. Pat. No. 006,855,695, 2005).

Following de-dialkyl-protection of 5 or 6 can readily convert to the corresponding phosphate free acid (7 or 8). For examples, de-protection of diethyl ester can be treated with trimethylsilyl bromide (TMSBr) (Matulic-Adamic, et al. *J Org Chem.* 1995, 60: 2563), de-protection of di-tert-butyl esters can be treated with trifluoroacetic acid (TFA) (Durgam, et al. *J Med Chem.* 2005, 48: 4919), and de-protection of di-TMSE esters cab be treated with TFA also (Dolye, et al. U.S. Pat. No. 006,458,816, 2002) or with $BF_3$-$Et_2O$ (Jansson, et al. Tetrahedron Lett. 1986, 27: 753). The phosphate free acid form 7 or 8 is purified by flash column chromatography (FCC) such as normal phase silica gel or reversed phase silica gel, and the desired SHP compound as drug substance is obtained after lyophilization.

Figure 4:
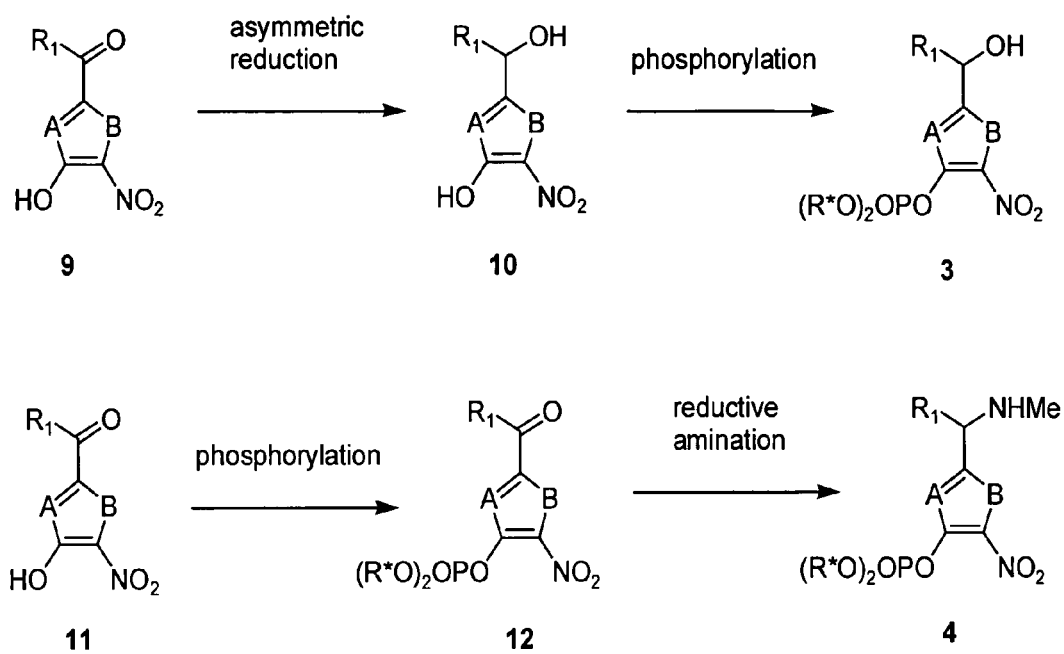

As shown in FIG. 4, the α-alkyl 4-nitroarylmethyl alcohol (3) can be synthesized from the corresponding alkyl aryl ketone (9), employing an enantiomerically selective reduction. A reducing catalyst can be selected from commercially available reagents such as 2-Me-CBS-oxazaborolidine/$BH_3$ (Mathre, et al. *J Org Chem.* 1993, 58: 2880) or diisopinocampheylchloroborane (Brown, et al. *J Am Chem Soc.* 1988, 110: 1539) or Alpine-borane (Ramachadran, et al. *Tetrahedron: Asymm.* 5: 1061). Asymmetric hydrogenation of the ketone also can be used (Ohkuma, et al. *J Am Chem Soc.* 1998, 120: 13529; and Baar, et al. *J Am Chem Soc.* 2004, 126: 8216).

The N-alkyl-N-(para-nitroarylmethyl)amine (4) can be prepared from the corresponding alkyl aryl ketone. For example, using sodium borohydride as a reducing agent, the reductive amination of a respective 12 with methylamine affords the corresponding N-arylmethyl-N-methylamine (4).

The hydroxyl group on the aryl ring can be reacted with chlorophosphate to give their corresponding di-alkyl-protected phosphonoxy-aryl compound (i.e. 3 or 12) under mild conditions. Selective phosphorylation of phenols was achieved with phosphite, carbon tetrachloride, DIPEA and catalytic amounts of 4-dimethylaminopyridine (DMAP) (Silverberg, et al. *Tetrahedron Lett.* 1996, 37: 771). It is common that the phosphorylation may complete prior to asymmetric reduction or the phosphorylation may follow reductive amination. The synthesis of the appropriate 4-nitroaryl compound (9 or 11) for use in these reaction schemes is well known in the art and uses standard chemical techniques such as nitration and acrylation.

After synthesis, the crude product generally is purified by reversed phase column chromatography and lyophylization. Treating KS119W (or VNP40541) with an appropriate alkaline solution or amine can readily provide a respective water-soluble salt such as sodium salt, tris(hydroxymethyl)-aminomethane (TRIS) salt, triethanolamine salt, triethylamine salt, or lutidine salt. Modification of the disclosed chemical synthetic methods may be readily made by those of ordinary skill in the art in order to provide alternative synthetic pathways to the present compounds.

Pharmaceutical compositions based upon the present novel chemical compounds comprise the above-described compounds in a therapeutically effective amount for the treatment of a condition or disease such as cancer, optionally in combination with a pharmaceutically acceptable additive, carrier or excipient.

Certain of the compounds, in pharmaceutical dosage form, may be used as prophylactic agents for preventing a disease or condition from manifesting itself.

The present compounds or their derivatives can be provided in the form of pharmaceutically acceptable salts. As used therein, the term pharmaceutically acceptable salts refers to appropriate salts of the active compounds according to the present invention which retain the desired biological activity of the parent compound. Nonlimiting examples of such salts include the sodium and potassium salts of phosphate, among others such as TRIS salt, triethanolamine salt, triethylamine salt, lutidine salt, or other pharmaceutically acceptable salts known in the art. Modifications of the active compound can affect the solubility, pharmacokinetic parameters and rate of metabolism of the active species, thus providing control over the delivery of the active species. Further, the modifications can affect the anticancer activity of the compound, in some cases increasing the activity over the parent compound. This can easily be assessed by preparing the derivatives and testing the anticancer activity according to known methods well within the routineer's skill in the art.

The compounds of this invention may be incorporated into formulations for all routes of administration including for example, parenteral and oral, including intravenous, intramuscular, intraperitoneal, intrabuccal, transdermal and in suppository form. Paranteral administration and in particular, intravenous or intramuscular administration is preferred.

Pharmaceutical compositions based upon these novel chemical compounds comprise the above-described compounds in a therapeutically effective amount for treating cancer and other diseases and conditions which have been described herein, optionally in combination with a pharmaceutically acceptable additive, carrier and/or excipient. One of ordinary skill in the art will recognize that a therapeutically effective amount of one of more compounds according to the present invention will vary with the infection or condition to be treated, its severity, the treatment regiment to be employed, the pharmacokinetics of the agent used, as well as the patient (animal or human) treated.

In the pharmaceutical aspect according to the present invention, the compound according to the present invention is formulated preferably in admixture with a pharmaceutically acceptable carrier. In general, it is preferable to administer the pharmaceutical composition parenterally and in particular, in intravenously or intramuscular dosage form, but a number of formulations may be administered via other parenteral routes, such as transdermal, buccal, subcutaneous, suppository or other route, including via an oral route of administration. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (such as salt formulation, etc.) which are well within the ordinary skill in the art. It is also well within the routineer's skill to modify the route of administration and dosage regimen of a particular compound in order to manage the pharmacokinetics of the present compounds for maximum beneficial effect to the patient.

The routineer will take advantage of favorable pharmacokinetic parameters of the prodrug forms of the present invention, where applicable, in delivering the present compounds to a targeted site within the host organism or patient to maximize the intended effects of the compound.

Administration of the active compound may range from continuous (intravenous drip), including bolus administration, intravenously or intramuscularly even less frequently than once a day to several administrations per day and may include topical, parenteral, intravenous, intramuscular, subcutaneous, transdermal (which may include a penetration enhancement agent), buccal and suppository administration, among other routes of administration, including, in certain instances, oral administration.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., intravenous or intramuscular. In preparing pharmaceutical compositions in the appropriate dosage form, any of the usual pharmaceutical media may be used. For parenteral formulations, the carrier may comprise sterile water or aqueous sodium chloride solution or dextrose 5% in water (D5W) in combination with other ingredients that aid dispersion, such as ethanol and other pharmaceutically acceptable solvents, including DMSO, among others. Of course, where solutions are to be used and maintained as sterile, the compositions and carriers must also be sterilized. Injectable suspensions may also be prepared, in which case appropriate liquid carriers, suspending agents and the like may be employed.

Solutions or suspensions used for parenteral, intradermal, subcutaneous, or topical application can be included the following components: a sterile diluent such as water for injection, saline solution, D5W solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as TRIS, acetates, citrates, phosphates, histidine or sodium bicarbonate solution; and agents for the adjustment of tonicity such as sodium chloride or dextrose. The parental preparation can be enclosed in ampoules, disposable syringes or multiple dose vials made of glass or plastic. If administered intravenously, preferred carriers include, for example, physiological saline or phosphate buffered saline (PBS).

In preparing pharmaceutical compositions in oral dosage form, any one or more of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric coated or sustained release by standard techniques.

In one embodiment, the active compounds may be prepared with a carrier that will protect the compound against rapid elimination from the body, such as a controlled release formulation, including implants and microencapsulated delivery system. Biodegradable, biocompatible polymers can be used, such as ethylene vinyl acetate, polyanhydrides, polyglycolic acid, collagen, polyorthoesters and polyactic acid. Methods for preparation of such formulations will be apparent to those skilled in the art.

Liposomal suspensions may also be pharmaceutically acceptable carriers. These may be prepared according to methods known to those skilled in the art. For example, liposome formulations may be prepared by dissolving appropriate lipid(s) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension. Other methods of preparation well known by those of ordinary skill may be used in this aspect of the present invention.

The present compounds may be used to treat animals, and in particular, mammals, including humans, as patients. Thus, humans, equines, canines, bovines and other animals, and in particular, mammals, suffering from tumors, and in particular, cancer, or other diseases as described herein, can be treated by administering to the patient an effective amount of one or more of the compounds according to the present invention or its derivative or a pharmaceutically acceptable salt thereof optionally in a pharmaceutically acceptable carrier or diluent, either alone, or in combination with other known pharmaceutical agents, depending upon the disease to be treated. This treatment can also be administered in conjunction with other conventional cancer therapies, such as radiation treatment or surgery.

The active compound is included in the pharmaceutically acceptable carrier or diluent in an amount sufficient to deliver to a patient a therapeutically effective amount for the desired indication, without causing serious toxic effects in the patient treated.

The present compounds are prodrug forms of reactive intermediates. In certain pharmaceutical dosage forms, the present compounds may be modified to other prodrug forms to take advantage of a particular route of administration of the active compounds. One of ordinary skill in the art will recognize how to readily modify the present compounds to alternative prodrug forms to facilitate delivery of active compounds to a targeted site within the patient. The individual of ordinary skill also will take advantage of favorable pharmacokinetic parameters of the prodrug forms, where applicable, in delivering the present compounds to a targeted site within the patient to maximize the intended anti-neoplastic effect of the compound.

The amount of compound included within the therapeutically active formulations according to the present invention is an effective amount for treating cancer. In general, a therapeutically effective amount of the compound according to the present invention in dosage form usually ranges from less than about 0.05 mg/kg to about 500 mg/kg of body weight of the patient to be treated, or considerably more, depending upon the compound used, the tumor type to be treated, the ability of the active compound to localize in the tissue to be treated, the route of administration and the pharmacokinetics of the compound in the patient. In the case of treating cancer, the compound is preferably administered in amounts ranging from about 0.05 mg/kg to about 250 mg/kg or more at one time. This dosage range generally produces effective blood level concentrations of active compound ranging from about 0.01 to about 500 micrograms per ml of blood in the patient to be treated. The duration of treatment may be for one or more days or may last for several months or considerably longer (years) depending upon the disease state treated. In a more preferred embodiment, the compound is given to the patient at doses of 0.1 mg/kg to 100 mg/kg, twice per day to once per 14 days, for the duration of 1 week to 52 weeks.

The concentration of active compound in the patient will depend on absorption, distribution, inactivation, and excretion rates of the drug as well as other factors known to those of skill in the art. It is to be noted that dosage given to the patient will be also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

The active compound according to the present invention can be also be mixed with other active materials that do not impair the desired action, or with materials that supplement the desired action, such as other anticancer agents, and in certain instances depending upon the desired therapy or target, antibiotics, antifungals, antiinflammatories, or antiviral compounds, among other agents.

These compounds according to the present invention are preferentially activated in hypoxic tumors and can be given either alone, or in combination with other anticancer agents or with phototheraphy or radiotherapy.

Compounds according to the present invention may be administered alone or in combination with other agents, especially including other compounds of the present invention. In these aspects according to the present invention, an effective amount of one or more of the compounds according to the present invention is co-administered along with an effective amount of at lease one additional anti-neoplastic/anticancer agent such as antimetabolites, etoposide, doxorubicin, taxol, vincristine, cytoxan (cyclophosphamide) or mitomycin C, among numerous others, including topoisomerase I and topoisomerase II inhibitors, such as adriamycin, topotecan, campothecin and irinotecan, other agent such as gemcitabine and agents based upon campothecin and cis-platin. In theory, the present compounds, which act by a mechanism to damage DNA, will act synergistically with compounds that act by a mechanism to reduce or prevent DNA repair. Thus, the present compounds may be advantageously combined with any compound which acts by a mechanism to reduce or prevent DNA repair, especially including inhibitors of enzymes which catalyze DNA repair, such as inhibitors of ribonucleotide reductase (RR) and inhibitors of $O^6$-alkylguanine-DNA alkyltransferase (AGT). By "co-administer" it is meant that the present compounds are administered to a patient such that the present compounds as well as the co-administered compound may be found in the patient's bloodstream at the same time, regardless of when the compounds are actually administered, including simultaneously. In many instances, the co-administration of the present compounds with traditional anticancer agents produces a synergistic (i.e., more than additive) result which is unexpected. In another embodiment, the compounds according to the present invention are given either simultaneously or sequentially with antibodies (conjugated or unconjugated), viruses, or bacteria. The antibodies, viruses, or bacteria could carry enzymes or gene encoding enzymes that activate the compounds described in the present invention. The enzymes include but not limit to NR.

While not being limited by way of theory, it is believed that the compounds according to the present invention primarily induce their therapeutic effect in treating malignant tumors by functional as hypoxia-selective chloroethylating agents.

Having generally described the invention, reference is now made to the following specific examples that are intended to illustrate preferred and other embodiments and comparisons. The included examples are not to be construed as limiting the scope of this invention as is more broadly set forth above and in the appended claims. Other compounds not specifically presented in the examples section of this application may be readily synthesized following analogous methodologies and/or facile syntheses that are presented and known in the art. One of ordinary skill may readily synthesize all compounds set forth and described without engaging in undue experimentation by simply following the detailed synthetic methodology directly or adapting/modifying such synthetic methodology using techniques well known in the art.

EXAMPLES

All reagents were purchased at commercial quality and used without further purification, and solvents were dried and/or distilled prior to use where necessary. All NMR spectra ($^1$H, $^{13}$C and $^{31}$P) were determined on a Bruker AC300 spectrometer. Chemical shifts are measured in parts per million (ppm) relative to tetramethylsilane. Coupling constants are reported in Hertz (Hz). Flash column chromatography (FCC) was performed with Merck silica gel 60 (230-400 mesh), and reserved phase column chromatography (RPCC) was packed with CAT gel (Water, preparative C-18, 125 Å, 55-105 μm) eluting with milli-Q de-ionized water.

Examples 1-2

Phosphorylation of Phenolic Compounds

General Procedure A. To a stirred solution of the appropriately phenolic compound (10.0 mmol) in acetonitrile (15 mL) was added DMAP (1 mmol) and DIPEA (20 mmol) at room temperature. The reaction mixture was cooled to −13° C. A solution of dialkyl chlorophosphate (10 mmol) in acetonitrile (5 mL) was added dropwise to maintain internal temperature at less than −10° C. The reaction mixture was raised to 0° C. and then kept stirring for 2 hours, monitoring reaction completion by TLC. The reaction mixture was concentrated by rotary evaporation, and the oil residue was worked up with dichloromethane and 0.5 M aqueous KHSO$_4$ solution. The organic layer was dried over anhydrous MgSO$_4$, then filtered and concentrated to brown viscous oil. The crude dialkylphosphonoxy-aryl compound could be used without further purification.

1-(3-Diethylphosphonoxy-4-notrophenyl)ethyl alcohol (13). Following the general procedure A, R-1-(3-hydroxy-4-nitrophaenyl)ethyl alcohol (18.2 g, 100 mmol) reacted with diethyl chlorophosphate (15.0 mL, 100 mmol), and the desired product 13 (32.0 g, 100%) was obtained.

$^1$H NMR (300 MHz, CDCl$_3$) δ 1.36 (t, J=7.1 Hz, 6H), 1.47 (d, J=6.6 Hz, 3H), 3.02 (br s, 1H), 4.25 and 4.27 (q, J=7.1 Hz, 4H), 4.91 (q, J=6.6 Hz, 4H), 7.26-7.31 (m, 1H), 7.55 (s, 1H), 7.90 (dd, J=8.5, 0.8 Hz, 1H).

$^{13}$C NMR (75 MHz, CDCl$_3$) δ 16.1 and 16.2, 25.3, 65.6 and 65.7, 68.8, 119.6, 122.2, 126.0, 140.0, 143.5 and 143.6, 154.4.

$^{31}$P NMR (121 MHz, CDCl$_3$) δ −6.7.

General Procedure B. A solution of phenolic compound (10 mmol), DIEA (20 mmol) and DMAP (1 mmol) in acetonitrile (20 mL) was placed in −50° C. bath. To the above cold solution was added CCl$_4$ (50 mmol) and dialkyl phosphite (10 mmol). The reaction solution was kept for 2 hours at room temperature. Then solvents were removed by rotary evaporation. The residue oil was worked up with 0.5 M aqueous KHSO$_4$ solution and dichloromethane. After separation, dry over anhydrous MgSO$_4$, evaporation and vacuum dry, the crude dialkylphosphonoxy-aryl compound could be used without further purification.

1-(3-Diethylphosphonoxy-4-notrophenyl)ethyl alcohol (13). Following the general procedure B, R-1-(3-hydroxy-4-nitrophaenyl)ethyl alcohol (15.0 g, 82.4 mmol) reacted with diethyl chlorophosphate (10.6 mL, 82.4 mmol), and the desired product 13 (27.1 g, 100%) was obtained.

Example 3

Grignard Reaction of Benzaldehydes

General Procedure. To a solution of 4-nitrobenzaldehydes (10 mmol) in anhydrous THF (30 mL) was slowly added Grignard reagent such as methylmagnesium bromide in diethyl ether (25 mmol) at −50° C. over 45 minutes. The temperature of the reaction mixture was maintained below −40° C. during the addition Grignard reagent. The reaction mixture was allowed to warm to room temperature and stirred for 3.5 hours. The reaction mixture was cooled to −10° C., and quenched with 5% hydrochloric acid (25 mL). The reaction mixture was diluted with water (25 mL) and the product was extracted with ethyl acetate (3×15 mL). The combined organic extracts were washed with water to pH 5, dried over anhydrous Na$_2$SO$_4$, filtered and concentrated. The residue was purified by flash chromatography on silica gel, eluting with 25% ethyl acetate in hexanes. After evaporated and dried in vacuum, the α-alkyl 4-notrobenzyl alcohol was obtained.

1-(3-Hydroxy-4-notrophenyl)ethyl alcohol (14). Following the general procedure, 3-hydroxy-4-nitrobenzaldehyde (90.0 g, 539 mmol) gave the desired product 14 (40.0 g, 41%) as red oil.

$^1$H NMR (300 MHz, CDCl$_3$) δ 1.50 (d, J=6.6 Hz, 3H), 2.06 (br s, 1H), 4.93 (q, J=6.3 Hz, 1H), 6.98 (dd, J=8.8, 1.9 Hz, 1H), 7.17 (d, J=1.7 Hz, 1H), 8.08 (d, J=8.8 Hz, 1H), 10.6 (s, 1H).

$^{13}$C NMR (75 MHz, CDCl$_3$) δ 25.3, 69.5, 116.3, 117.6, 125.5, 155.5, 156.9.

Example 3

Reduction of Acetophenones

General Procedure. To a solution of the A solution of chiral (R or S)-2-methyl-CBS-oxazaborolidine (1.0 M solution in toluene, 240 mL) and 1.0 M BH$_3$-THF solution (120 mL) was cooled to −50° C. To the above solution was slowly added a solution of 3'-hydroxy-4'-nitroacetophenone (100 g) in THF/toluene (200 mL/800 mL) and 1.0 M BH$_3$-THF solution (1.0 L) simultaneously over 4 hours, while stirring vigorously. The reaction mixture was kept stirring at −50° C. for 2-3 hours, monitoring reaction completion by HPLC. Then, acetone (200 mL) was dropwise charged into the reactor at −50° C. After stirred at −50° C. for 10 minutes, the reaction mixture was allowed to warm up to ambient temperature and stir for 1.5 hours. Concentrated by rotary evaporation on 45° C. bath, the residue was treated with saturated Na$_2$CO$_3$ aqueous solution (2 L). The mixture was heated at 50° C. for 30 min, and then cooled down to room temperature. Added tert-butylmethylether (TBME, 1 L) and hexanes (1 L), the mixture was stirred at RT for 1 hour and then separated. The aqueous layers were charged concentrated HCl dropwise to adjust pH 6, while maintaining temperature at 25° C. The mixture was extracted with ethyl acetate (3×2 L), and the organic phases were concentrated. Crude product was afforded as brown oil, and was purified by re-crystallization from hexanes.

R-1-(3-Hydroxy-4-nitrophenyl)ethyl alcohol (15). Following the general procedure, 3-hydroxy-4-nitroacetophenone (100 g, 0.55 mol) gave the desired product 15 (52 g, 51%, 99.3% ee) as yellow solid.

Example 5

Reductive Amination of Benzaldehydes

General Procedure. To a solution of benzaldehyde (10 mmol) in dichloromethane (10 mL) was added 2 N solution of methylamine in THF (20 mmol). The reaction solution was kept at room temperature overnight and the precipitate was filtered. The filtrate was concentrated and dried in vacuum, and the resulting crude oil was dissolved in methanol (50 mL). To the above solution was added NaBH$_4$ (20 mmol) in small portions at 0° C., and the solution was kept stirring continuously for 4 hours. After evaporation, the residue was distributed in water (50 mL) and dichloromethane (50 mL). The aqueous phase was separated and extracted with dichloromethane (50 mL) once. The combined organic phases were dried over anhydrous MgSO$_4$, filtered, concentrated and dried in vacuum. Crude N-benzyl-N-methylamine was pure enough for use without further purification.

N-(4-Diethylphosphonoxybenzyl)-N-methyl amine (16). Following the general procedure, diethylphosphonoxy-benzaldehyde (29.9 g, 116 mmol) gave 15 (22.3 g, 71%) as yellow oil.

$^1$H NMR (300 MHz, CDCl$_3$) δ 7.31 (d, J=8.0 Hz, 2H), 7.17 (d, J=8.5 Hz, 2H), 4.21 (m, 4H), 3.73 (s, 2H), 2.42 (s, 3H) and 1.34 (t, J=6.9 Hz, 6H).

$^{13}$C NMR (75 MHz, CDCl$_3$) δ 149.4 (d), 135.6, 129.3, 119.5 (d), 64.2 (d), 54.5, 35.1 and 15.7 (d).
$^{31}$P NMR (121 MHz, CDCl$_3$) δ −5.5.

Examples 6-7

Phosgene Coupling Reaction

General Procedure A. To a stirred solution of 90CE (10 mmol) in acetonitrile (40 mL) was added phosgene (20% in toluene, 10 mmol) and DIPEA (10 mmol). Kept at 0° C. for 20 minutes, to the solution was added N-(dialkylphosphonoxy-benzyl)-N-methylamine (10 mmol) and DIEA (10 mmol). The final reaction solution was kept at 5° C. overnight. After evaporation, the residue was worked up with water and dichloromethane. The combined organic phases were dried over anhydrous MgSO$_4$, filtered and evaporated. The corresponding protected phosphate was obtained as oil.

General Procedure B. DIPEA (12 mmol) was added to a 20% solution of phosgene in toluene (30 mmol) at 0° C. A solution of 1-(3-diethylphosphonoxy-4-notrophenyl)ethyl alcohol (10 mmol) in acetonitrile (15 mL) was added slowly. The reaction mixture was stirred at room temperature for 2 hours and then concentrated. The residue was dissolved in acetonitrile (15 mL), DIPEA (15 mmol) and 90CE (10 mmol) was added while cooling below 20° C. The mixture was stirred at room temperature for 2 hours. After evaporated solvents, the residue was worked up with water and dichloromethane. The organic phases were washed with 1% HCl solution (35 mL), dried over anhydrous MgSO$_4$, and evaporated to dryness. The residue was purified by flash chromatography on silica gel (eluting with 40-50% ethyl acetate in hexanes), concentrated and dried under high vacuum to give the corresponding protected phosphate was obtained as oil.

1,2-Bis(methylsulfonyl)-2-(2-chloroethyl)hydrazine-carboxylic acid 1-(3-diethylphosphonoxy-4-nitrophenyl)ethyl ester (16). Following the general procedure B, 1-(3-diethylphosphonoxy-4-notrophenyl)ethyl alcohol (114.3 g, 358 mmol) yielded 16 (151.2 g, 71%).

$^1$H NMR (300 MHz, CDCl$_3$) δ 1.30-1.42 (m, 6H), 1.69 and 1.70 (d, J=6.6 Hz, 3H), 3.16 and 3.21 (s, 3H), 3.46 and 3.47 (s, 3H), 3.65-3.75 (m, 2H), 3.80-3.92 (m, 1H), 4.00-4.10 (m, 1H), 4.20-4.35 (m, 4H), 5.95 and 5.96 (q, J=6.6 Hz, 1H), 7.34 and 7.36 (d, J=8.2 Hz, 1H), 7.60 and 7.65 (s, 1H), 7.96 and 7.97 (d, J=8.5 Hz, 1H).
$^{31}$P NMR (121 MHz, CDCl$_3$) δ −6.7.

Example 8

Formation of Phosphate Free Acid

General Procedure. A solution of the respective diethyl-protected phosphate (10 mmol) in dichloromethane (60 mL) was treated with excess TMSBr (100 mmol) at 5° C. overnight. Evaporated and dried in vacuum, the crude phosphate free acid was obtained as a glassy solid. To the crude compound (10 mmol) was added water (about 30 mL). The suspension was stirred for 2 hours at ambient temperature, and then a minimum amount of water was added to complete dissolution. The aqueous solution was purified by RPCC with 10% acetonitrile in de-ionized water. The fractions were monitored by UV or $^{31}$P NMR and combined. After lyophilization, the purified phosphate free acid was obtained as a white or off-white powder.

1,2-Bis(methylsulfonyl)-2-(2-chloroethyl)hydrazine-carboxylic acid 1-(3-dihydrogenphosphonoxy-4-nitrophenyl) ethyl ester (17). Following the general procedure, 1,2-bis (methylsulfonyl)-2-(2-chloroethyl)hydrazine-carboxylic acid 1-(3-diethylphosphonoxy-4-nitrophenyl)ethyl ester (73.9 g, 124 mmol) was de-protected and yielded 17 (52.8 g, 80%) as a white powder.

$^1$H NMR (300 MHz, DMSO-d$_6$) δ 1.58 and 1.59 (d, J=6.1 Hz, 3H), 3.25 and 3.29 (s, 3H), 3.54 and 3.55 (s, 3H), 3.65-3.83 (m, 2H), 3.85-4.00 (m, 2H), 5.97 and 5.99 (q, J=6.1 Hz, 1H), 7.42 (d, J=8.2 Hz, 1H), 7.60 and 7.65 (s, 1H), 7.96 and 7.97 (d, J=8.4 Hz, 1H).
$^{31}$P NMR (121 MHz, DMSO-d$_6$) δ −5.6.

Example 9

Formation of Phosphate Salts

General Procedure. A solution of the KS119W (200 mg) and a base as upon stoichiometry is dissolved in water (2.0 mL) and stirred at 20° C. for 1 hour; the solution is lyophilized for 20 hours; and the resulting solid is then analyzed by NMR and HPLC.

Monosodium salt of KS119W (18). A 5% NaHCO$_3$ solution (210 mL) was slowly added to a stirred solution of KS119W (66.1 g, 122.4 mmol) in methanol (70 mL) and water (400 mL) until a pH of 4.0 to 4.5 is obtained. The reaction mixture was washed with dichloromethane (2×500 mL) followed by diethyl ether (200 mL) to remove the decomposition impurity. The aqueous portion was concentrated below a temperature of 30° C. The residue was dissolved in acetone (200 mL) and slowly added to a cold (10° C.) diethyl ether (2.0 L) with efficient stirring. The resulting slurry was stirred at 0° C. for 1 hour, filtered, washed with diethyl ether (200 mL) and then hexanes (200 mL) and dried to give a light yellow solid 18 (109.7 g, 86%).

$^1$H NMR (300 MHz, D$_2$O) δ 1.37 and 1.38 (d, J=6.6 Hz, 3H), 2.91 and 3.00 (s, 3H), 3.24 and 3.25 (s, 3H), 3.30-3.50 (m, 2H), 3.55-3.75 (m, 2H), 5.69 and 5.70 (q, J=6.6 Hz, 1H), 7.06 (d, J=8.1 Hz, 1H), 7.24 and 7.25 (s, 1H), 7.65 (d, J=8.4 Hz, 1H).
$^{13}$C NMR (75 MHz, DMSO-d$_6$) δ 22.5, 41.2, 41.3, 41.8, 41.9, 42.5, 42.6, 52.9, 53.1, 77.1, 77.2, 118.6, 118.8, 120.0, 120.2, 124.9, 141.5, 145.8, 145.9, 147.7, 147.8, 151.4.
$^{31}$P NMR (121 MHz, DMSO-d$_6$) δ −4.09.

Example 10

Determination of Solubility and Stability in Aqueous Solutions

The solubility of KS119W (or VNP40541) was determined visually by adding incremental quantities of the drug to 2.0 mL of water in a glass vial. The vials were shaken at room temperature in a Glas Col rotary apparatus until the drug dissolved entirely. Additional fixed quantities of drug were added and the vials shaken until complete dissolution. This process was continued until no more drug dissolved. The solubility of KS119W (or VNP40541) was found to be more than 400 mg/mL. Aqueous solutions of VNP40541 (or VNP40541) were light yellow.

The solubility of the newly synthesized KS119W salts was similarly determined by adding an excess amount of the drug in a glass vial containing 2.0 mL of water. The vials were shaken in a Glas Col rotary apparatus at room temperature for 24 hours. The suspension containing undissolved drug was centrifuged; the supernatant was carefully separated and analyzed by HPLC for drug concentration. Water-solubility (mg/ mL) of the KS119W salts from Mg(OH)$_2$, NaOH, KOH, BET, and TRIS is detected: 51.2, 67.2, 71.0, 58.7, and 70.5, respectively.

The stabilities of VNP40541 were investigated. The sample (20 mg/mL) was dissolved in 20 mM citric acid and titrated to pH 2.0, pH 3.0, pH 4.0, pH 5.0, pH 6.0, and pH 7.0. To control for buffer catalysis, the drug was also titrated to pH 2.0, pH 5.0, and pH 6.0 in the absence of citrate. The samples were stored at 40° C. for 3 hours, 24 hours, and 3 days, and at room temperature for 24 hours, 3 days. Upon completion of each time point, samples were placed in a freezer at −15° C. Control samples of each preparation were also stored in the freezer. Each sample was analyzed by HPLC repetitively, at various time points, to determine the concentration of the respective drug. As demonstrated in Table 1 below, the results indicate clearly that significant degradation was observed after 24 hours at 40° C. The presence of citrate did not appear to affect degradation significantly.

TABLE 1

Short term stability of VNP40541 as a function of pH and presence of citrate buffer. HPLC assay results are expressed relative to control samples stored at −15° C..

|  |  | 24 hrs Room Temp. | | 3 hrs 40° C. | | 24 hrs 40° C. | |
| --- | --- | --- | --- | --- | --- | --- | --- |
| pH | Citrate | Final pH | Assay | Final pH | Assay | Final pH | Assay |
| 2.0 | 20 mM | 2.00 | 99.3% | 2.00 | 98.8% | 2.02 | 92.3% |
| 2.0 | None | 2.04 | 99.4% | 2.04 | 98.9% | 2.06 | 91.7% |
| 3.0 | 20 mM | 3.07 | 99.3% | 3.07 | 98.9% | 3.06 | 91.3% |
| 4.0 | 20 mM | 4.08 | 100.1% | 4.07 | 99.8% | 4.09 | 92.2% |
| 5.0 | 20 mM | 5.03 | 99.4% | 5.04 | 98.8% | 5.06 | 92.2% |
| 5.0 | None | 5.12 | 99.7% | 5.14 | 99.4% | 5.10 | 92.5% |
| 6.0 | 20 mM | 6.17 | 98.6% | 6.16 | 99.0% | 6.10 | 93.8% |
| 6.0 | None | 6.09 | 100.0% | 6.10 | 99.3% | 6.01 | 93.8% |
| 7.0 | 20 mM | 7.07 | 99.7% | 7.06 | 99.6% | 6.96 | 94.0% |

Example 11

Aerobic/Hypoxic Cell Survival Studies

EMT6 or CHO (parental or human cytochrome P-450 reductase transfected) cells, seeded in glass milk dilution bottles, were gassed for 2 hours through a rubber septum fitted with 13 gauge (inflow) and 18 gauge (outflow) needles with a mixture of 5% CO$_2$, oxygen at various concentrations, with the balance of the mixture made up of nitrogen, to establish various hypoxic conditions. Drugs were then injected without disrupting hypoxia. After two hours, cells were collected and plated in a clonogenic assay to determine the surviving fraction, compared to untreated controls.

For in vitro analysis, KS119W must be converted to KS119OH (1) in an AP-catalyzed reaction shown above in FIG. 2, as the phosphorylated parent drug cannot cross cell membranes. KS119OH is then used in all subsequent in vitro studies shown in this section.

Figure 5:
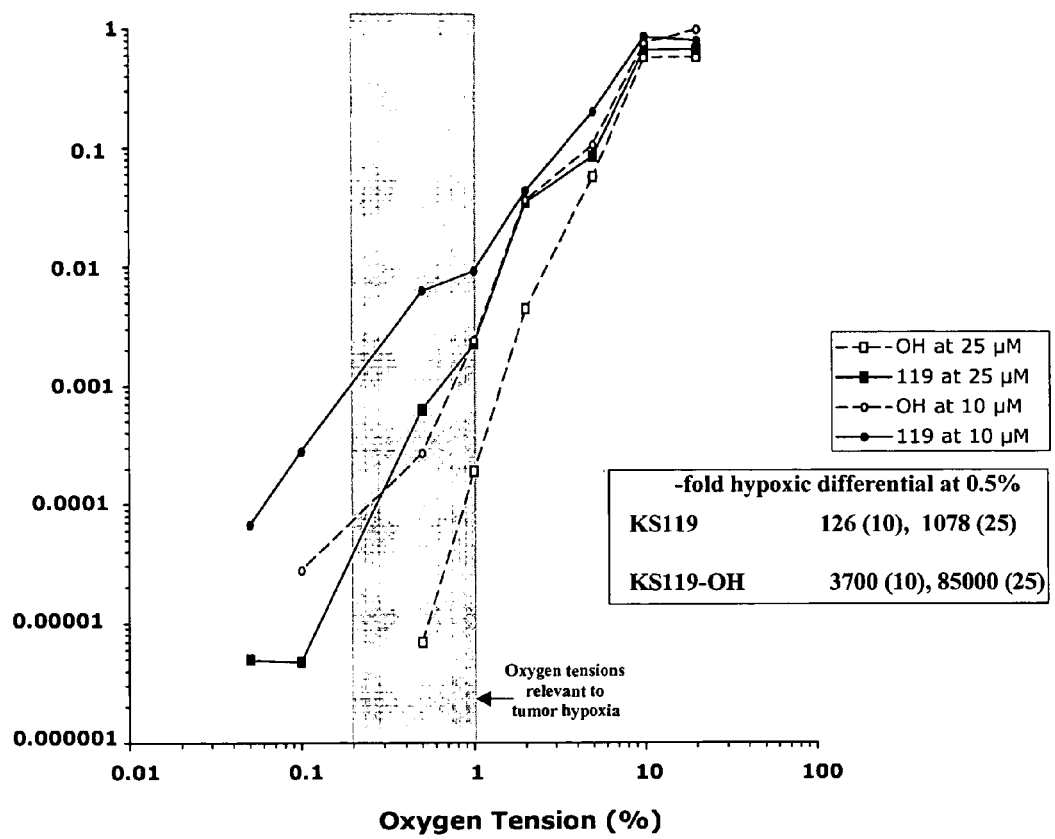
FIGS. 5 to 7 are representations of experimental results which are presented in the present application related to the selective activation in hypoxic conditions according to the present invention.

EMT6 murine mammary carcinoma cells were exposed to graded concentrations of KS119 or KS119OH at oxygenation levels reflecting normal air (21% oxygen) or a severely hypoxic atmosphere composed of 0.1% oxygen. The results, shown in FIG. 5, demonstrate that both drugs are virtually inactive under oxygenated conditions, with very little cytotoxicity to EMT6 cells at concentrations of drug up to 25 μM. At 0.1% oxygen, both drugs display potent cytotoxic effects with cell kill approaching 5 orders of magnitude at 10 μM drug concentration.

Figure 6:
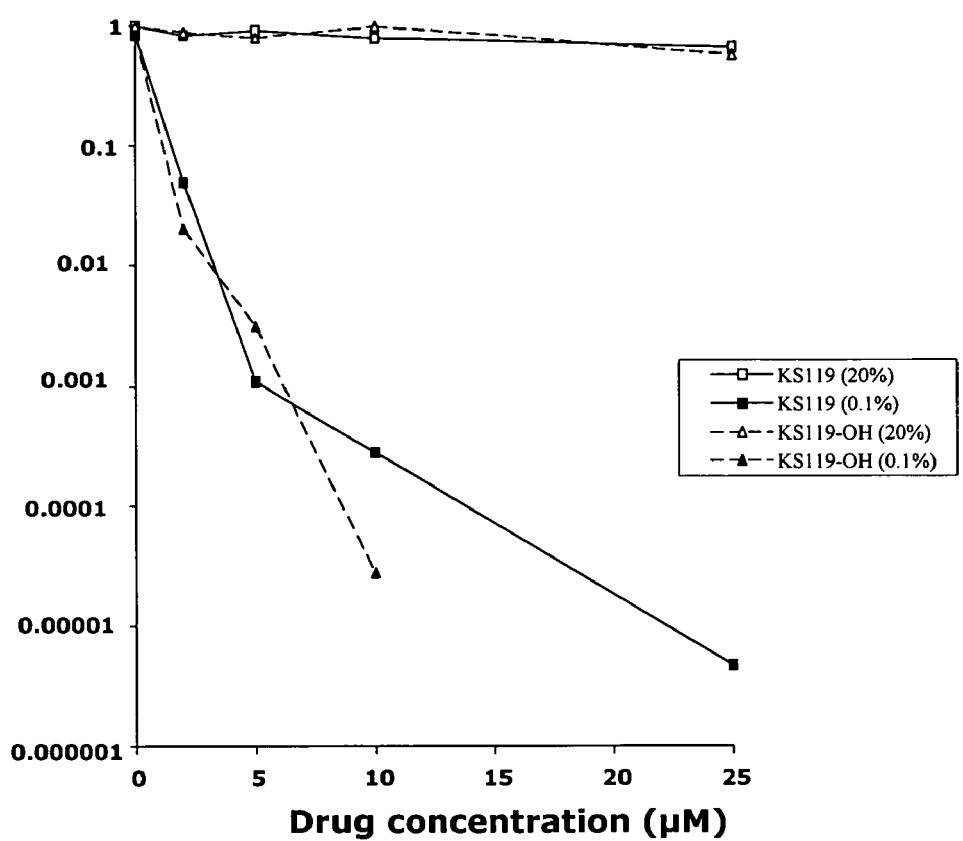

Similarly, EMT6 cells were exposed to 10 or 25 μM of KS119 and KS119W-OH at graded concentrations of oxygen ranging from 0.05% to 21% to demonstrate drug activity as a function of oxygen concentration. The results, shown in FIG. 6, demonstrated significant drug activity at all oxygen concentrations below 10% oxygen, with considerable activity at oxygen concentrations that have been measured in solid tumors (shaded bar).

Moreover, the R- and S-enantiomers of KS119W (VNP40541 and VNP40551) were converted to the corresponding de-phosphorylated forms for study in the in vitro aerobic/hypoxic cell assay. The results demonstrated that the in vitro cytotoxic activity of R-KS119OH and S-KS119OH to EMT6 cells is very similar to the parental racemic drug with respect to both potency and aerobic/hypoxic differential.

As illustrated in FIGS. 1 and 2, KS119OH (1) like KS119 can be reduced under hypoxic conditions by one-electron reductases like cytochrome P-450 reductase to generate an intermediate of hydroxylamine or aniline (2), which spontaneously liberate the DNA alkylating and cytotoxic species, 90CE. To demonstrate that KS119W (racemic and two enantiomers) could be activated by cytochrome P-450 reductase under hypoxia, CHO cells transfected for and overexpressing this reductase were exposed to the drugs, and the sensitivity of this cell line to these agents was compared to the non-transfected parental line expressing low, basal levels of enzyme. The results, displayed in Table 2, demonstrate that cytochrome P-450 reductase sensitized the CHO cell line to all three agents only under hypoxia approximately equally. Like KS119, cytochrome P-450 reductase can activate KS119OH under hypoxic conditions.

TABLE 2

Effect of Cytochrome P-450 Reductase Expression on R-, S-, and Racemic KS119OH Cytotoxicity

| Drug (10 μM) | VNP40541 | VNP40551 | KS119W |
| --- | --- | --- | --- |
| | Surviving fraction at 0.1% oxygen | | |
| CHO-SCS-II | 0.04737 | 0.1188 | 0.3336 |
| CHO-450red | 0.001368 | 0.002553 | 0.009444 |
| | Surviving fraction in air | | |
| CHO-SCS-II | 1.086 | 1.148 | 1.185 |
| CHO-450red | 0.9277 | 1.015 | 0.8791 |

Example 13

Evaluation of In Vivo Anti-tumor Activity

The anti-tumor effects of aforementioned prodrugs are evaluated in both solid and liquid tumor models, including the B16-F10 murine melanoma, HTB177 human lung carcinoma models, DLD1 human colon carcinoma, EMT-6 murine mammary gland carcinoma, L1210 murine leukemia, lymphoma, prostate cancer, pancreatic cancer, and head-and-neck cancer. The prodrugs are given intravenously, orally, or intraperitoneally at doses from 10 mg/kg to 2000 mg/kg; they are give at different dosing schedules such as 4 times daily, once daily, or once every several days for up to 60 doses. Testing tumor cells were implanted subcutaneously into mice, which were randomized into groups immediately after tumor cell implantation (Day 0). Mice were injected intraperitoneally (ip) with either a bolus injection of 0.1 mL PBS or drug. The treatment was carried out in a designed dosing schedule. Tumor measurement in three dimensions was determined once a week with the formula L×H×W/2, where L, H, and W represent length, height, and width, respectively. The toxicity of these drugs in mice was mild as determined by body weight loss and animal appearance.

Efficacy of KS119 was studied in murine tumor model and human xenograft models. EMT-6 murine mammary carcinoma cells ($3 \times 10^5$ cells/mouse) were implanted subcutaneously into Balb/c mice. H460 human lung carcinoma cells, HT29 human colon carcinoma cells and SHP77 human lung carcinoma cells were established as solid xenografts in nu/nu CD-1 mice and Scid/Beige mice with $7 \times 10^7$ cells/mouse, respectively. After implantation, tumors were allowed to grow to a size of 150 to 200 mm$^3$ before starting treatment with KS119. KS119 was formulated in a solvent containing polyethylene glycol 300 (PEG), ethyl alcohol, citric acid, and ascorbic acid.

Figure 7:
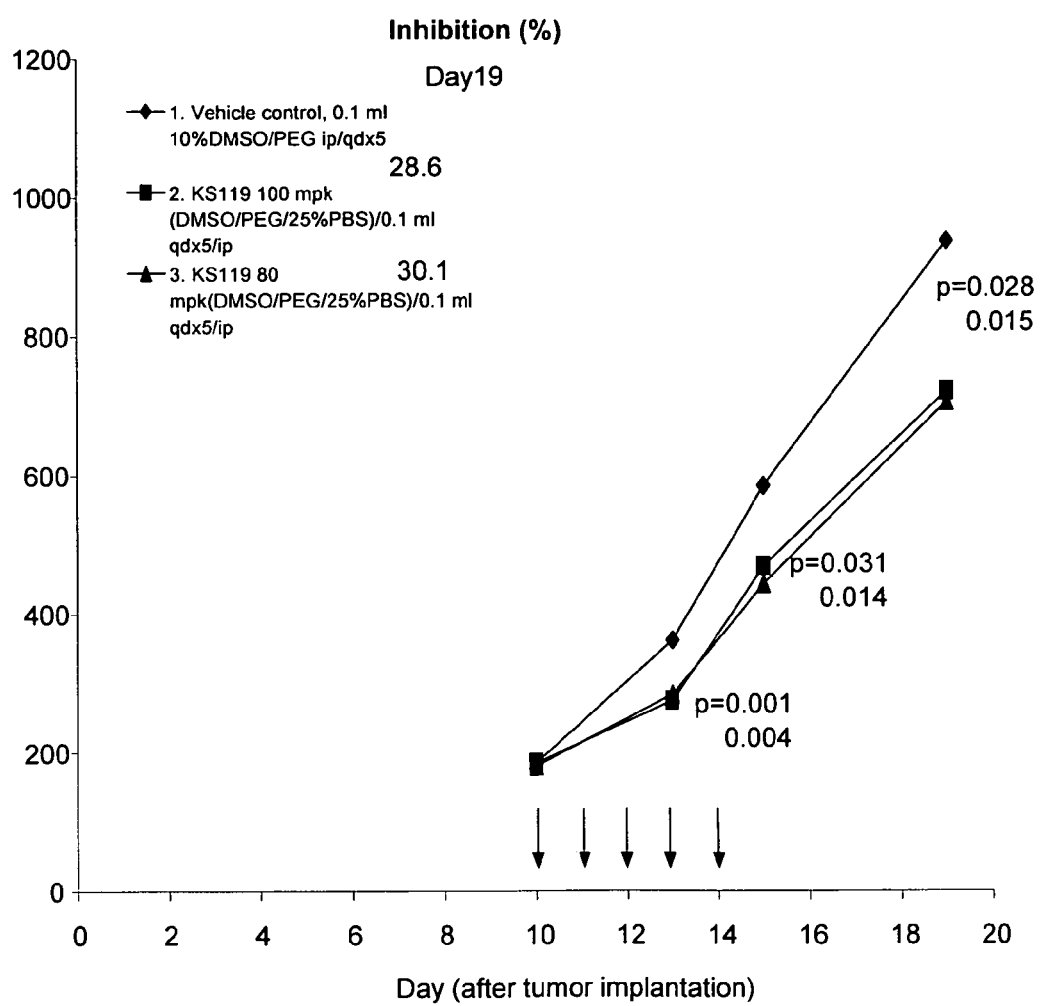

The result of representative studies by daily ip administration of KS119 at doses of 80 and 100 mg/kg was shown in FIG. 7. The data indicated that KS119 produced a marginal but statistically significant antitumor effect against all of tumor models tested. The inhibition of KS119 on the growth of all tumors tested was ranged 30 to 50%. The inhibitions were significantly (p<0.05) when compared with vehicle controls.

Figure 8:
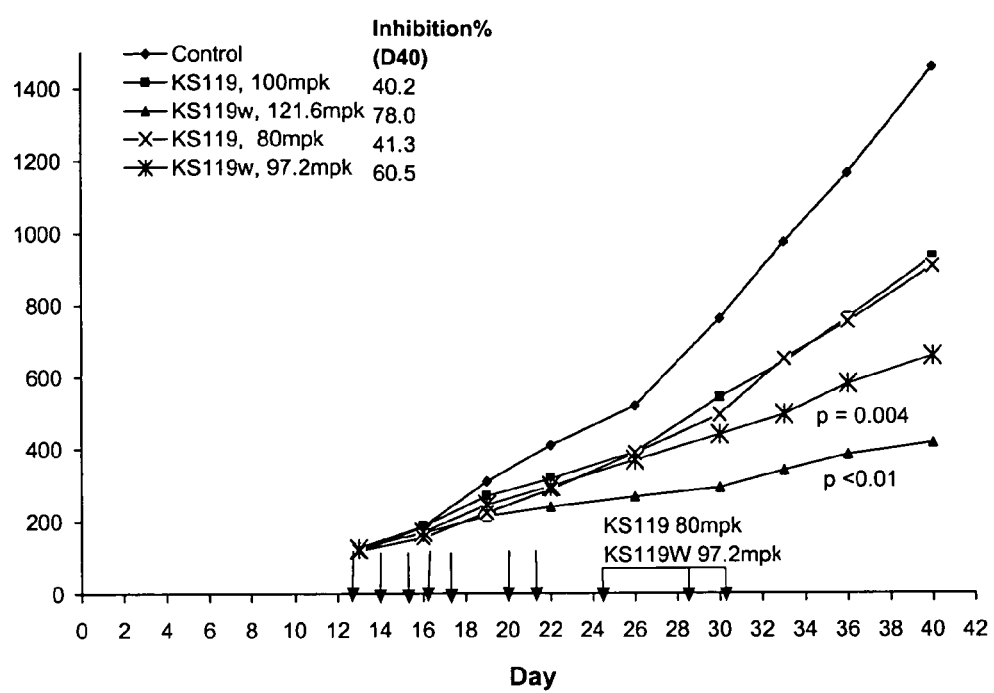
FIGS. 8 to 9 are representations of experimental results which are presented in the present application related to the efficacy and toxicity of certain preferred embodiments according to the present invention.

Efficacies of KS119W and KS119 were compared with equivalence molar doses in EMT-6 tumor and H460 tumor models. KS119W was formulated with 0.25M sodium bicarbonate solution. The treatment was started when tumors researched 150 to 200 mm$^3$, and lasted up to 2 weeks. KS119 at doses of 80 and 100 mg/kg and KS119W at doses of 97.6 and 121.3 mg/kg were daily administrated into mice via ip injection. As showed with an example of H460 tumor (FIG. 8), KS119 and KS119W both inhibited the growths of tumor in mice. In comparison with KS119 at equal molar doses, KS119W was clearly more effective and produced greater antitumor activity. The final tumor volumes in the groups treated with 121.6 mg/kg, ×7 doses and 97.2 mg/kg ×10 doses of KS119W were reduced 78% and 60%, respectively, compared with those in the control group; whereas the groups treated with equal molar doses of KS119 at 100 mg/kg and 80 mg/kg reduced only 40% inhibition. The toxicity of KS119 and KS119W were dose-dependent. To assess the toxicity of treatment, body weight and peripheral blood cell count were monitored after treatment. There was not significant hematological toxicity or severe weight loss in the mice treated with both drugs at the doses described above.

In order to fairly select a better compound from two enantiomers of KS119W for future clinical development, finding maximum tolerated dose (MTD) for VNP40541 (R-form) and VNP40551 (S-form) was conducted and the results were shown as Table 3.

TABLE 3

MTD Findings for Comparison between Two Enantiomers

| Mice | Nude CD-1 | BALB/c | Scid/Beige |
|---|---|---|---|
| VNP40541 | 140 mpk × 10 | 100 mpk × 5 | 110 mpk × 8 |
| VNP40551 | 80 mpk × 10 | 85 mpk × 5 | 85 mpk × 8 |

As illustrated in Table 4, VNP40541 and VNP40551 were evaluated in three sample tumor models in mice. Thus, they had exhibited quite similar efficacies and therapeutic windows, however VNP40541 had clearly demonstrated lower toxicity, particularly having less edema observed.

TABLE 4

Efficacies and Therapeutic Windows between Enantiomers

| | H460/Nude Mice | | EMT6/BLAB-c Mice | | SHP77/Scid-Beige | |
|---|---|---|---|---|---|---|
| | Dose (mpk) | Inhibition (%) | Dose (mpk) | Inhibition (%) | Dose (mpk) | Inhibition (%) |
| VNP40541 | 80-140 | 52-80 | 85-115 | 58-69 | 110 | 83 |
| VNP40551 | 40-80 | 53-80 | 55-85 | 52-78 | 85 | 82 |

Figure 9:
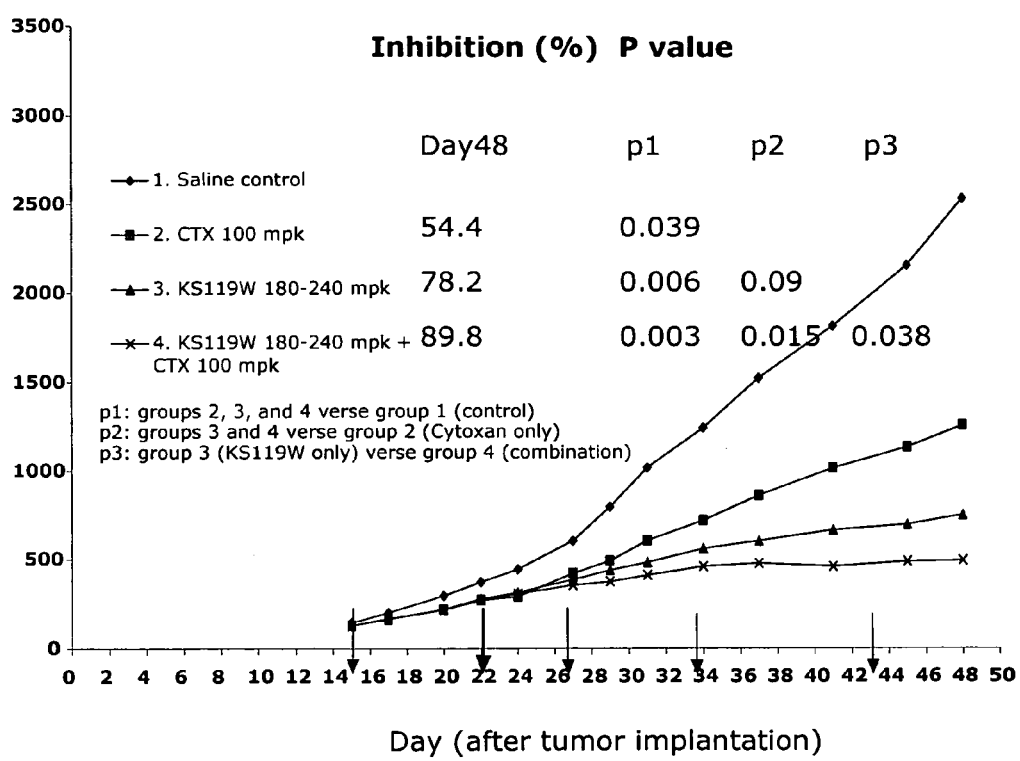

Combined therapy of KS119W with cytoxan (CTX) was evaluated by using KS119W at dose below the MTD in combination with nontoxic dose of CTX against EMT-6 murine mammary carcinoma and H460 human lung carcinoma in CD-1 nude mice. The tumors were allowed to grow to a size of approximately 200 mm$^3$. In H460 tumor model, the animals received either with 4 doses 180 mg/kg and 1 dose 240 mg/kg of KS119 or CTX at dose of 100 mg/kg per dose per animal, ip injecting the drugs on 15, 22, 27, 34 and 43 days after the tumor implantation. In the combination studies, CTX was given two hours after dosing KS119W. As showed on FIG. 9, KS119W alone resulted in 78% tumor growth inhibition, whereas CTX produced 54% inhibition only. The combination treatment of KS119W and CTX resulted in 90% tumor growth inhibitory. The inhibition of combination therapy was statistically significant against all control groups with p values of 0.003, 0.015 and 0.038, respectively. Additive toxicity at the doses used for combination was manageable; while the 180 mg/kg qw ×4 doses of KS119W alone caused a maximum net body weight loss of 4.5%, the same dose in combination with 4 doses of CTX at 100 mg/kg per week caused 8.6% weight loss but no death. A similar degree of growth inhibition was also observed with EMT-6 tumor model. Treatment of KS119W at dose of daily 97 mg/kg for 7 doses resulted in 59% tumor inhibition, and CTX at dose of 100 mg/kg, ip once per week for 4 doses generated a negligible effect on the tumor growth of EMT-6 in mice. Marked antitumor effects were observed when animals treated with a combination of KS119 and CTX. KS119W and CTX combination resulted in 91.8% growth inhibition of EMT-6 tumor. These results shows agent KS119W in combined with CTX have additive antitumor efficacy.

It is to be understood by those skilled in the art that the foregoing description and examples are illustrative of practicing the present invention, but are not in no way limiting. Variations of the detail presented herein may be made without departing from the spirit and scope of the present invention as defined by the following claims.

What is claimed is:

1. A compound according to the chemical structure:

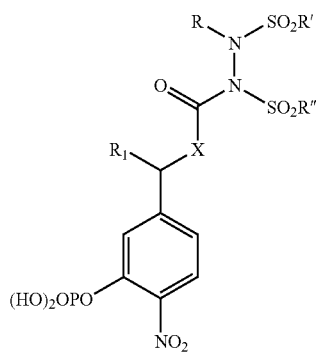

where R is $C_1$-$C_{10}$ alkyl or haloalkyl;

R' and R" are each independently $C_1$-$C_{10}$ alkyl;

$R^1$ is $CH_3$; and

X is O;

or a pharmaceutically acceptable salt, or enantiomer, thereof.

2. The compound according to claim 1 wherein R is $CH_3$, $CH_2CH_3$ or a $C_2$-$C_3$ haloalkyl or a pharmaceutically acceptable salt or enantiomer thereof.

3. The compound according to claim 1 wherein R' and R" are $C_1$-$C_3$ alkyl or a pharmaceutically acceptable salt or enantiomer thereof.

4. The compound according to claim 1 wherein R is a $CH_2CH_2Cl$ group and R' and R" are $CH_3$, or a pharmaceutically acceptable salt or enantiomer there of.

5. The compound according to claim 4 according to the chemical structure:

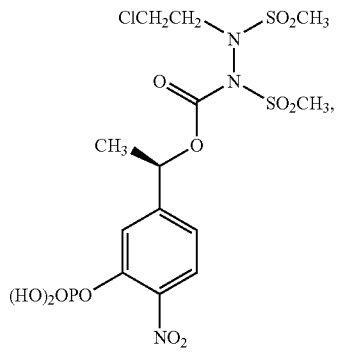

or a pharmaceutically acceptable salt thereof.

6. The compound according to claim 4 according to the chemical structure:

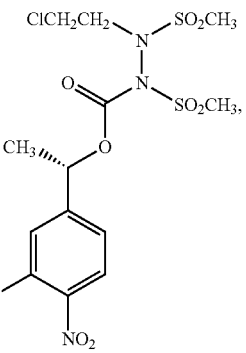

or a pharmaceutically acceptable salt thereof.

7. A pharmaceutical composition comprising a compound according to claim 1 in combination with a pharmaceutically acceptable carrier, additive or excipient thereof.

8. A pharmaceutical composition comprising an anti-cancer effective amount of a compound according to claim 2 in combination with a pharmaceutically acceptable carrier, additive or excipient thereof.

9. pharmaceutical composition comprising an anti-cancer effective amount of a compound according to claim 3 in combination with a pharmaceutically acceptable carrier, additive or excipient thereof.

10. A pharmaceutical composition comprising an anti-cancer effective amount of a compound according to claim 4 in combination with a pharmaceutically acceptable carrier, additive or excipient thereof.

11. A compound having the chemical structure:

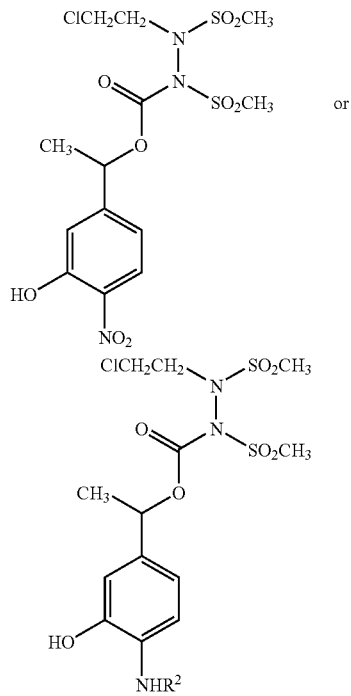

where $R^2$ is H or OH.

* * * * *